US008617077B2

(12) United States Patent
van Groningen et al.

(10) Patent No.: US 8,617,077 B2
(45) Date of Patent: Dec. 31, 2013

(54) ULTRASOUND APPLICATION DEVICE

(75) Inventors: Johannis van Groningen, Oude Tonge (NL); Petrus Alfonsus Maria Roodink, Hellevoetsluis (NL)

(73) Assignee: Enraf-Nonius B.V., Rotterdam (NL)

( * ) Notice: Subject to any disclaimer, the term of this patent is extended or adjusted under 35 U.S.C. 154(b) by 0 days.

(21) Appl. No.: 13/051,029

(22) Filed: Mar. 18, 2011

(65) Prior Publication Data

US 2011/0230794 A1 Sep. 22, 2011

(30) Foreign Application Priority Data

Mar. 19, 2010 (EP) ................................... 10157051

(51) Int. Cl.
*A61B 8/14* (2006.01)

(52) U.S. Cl.
USPC .......................................... 600/459; 600/439

(58) Field of Classification Search
USPC ................................... 600/437–469; 601/1–4
See application file for complete search history.

(56) References Cited

U.S. PATENT DOCUMENTS

| 5,158,087 | A | * | 10/1992 | Gatzke | .......................... | 600/459 |
| 5,261,427 | A | * | 11/1993 | Dolev | ............................ | 132/200 |
| 5,460,595 | A | * | 10/1995 | Hall et al. | .......................... | 601/2 |
| 5,545,942 | A | | 8/1996 | Jaster et al. | | |
| 5,776,065 | A | * | 7/1998 | Mehmanpazir et al. | ....... | 600/437 |
| 5,961,465 | A | | 10/1999 | Kelly, Jr. et al. | | |
| 6,217,530 | B1 | * | 4/2001 | Martin et al. | ...................... | 601/2 |
| 6,287,305 | B1 | * | 9/2001 | Heim et al. | ........................ | 606/41 |
| 6,500,133 | B2 | * | 12/2002 | Martin et al. | ...................... | 601/3 |
| 7,303,530 | B2 | * | 12/2007 | Barnes et al. | ................. | 600/459 |
| 7,967,764 | B2 | * | 6/2011 | Lidgren et al. | .................... | 601/3 |
| 2004/0171970 | A1 | | 9/2004 | Schleuniger | | |
| 2005/0054954 | A1 | * | 3/2005 | Lidgren et al. | .................... | 601/2 |
| 2006/0149169 | A1 | | 7/2006 | Nunomura et al. | | |
| 2007/0167814 | A1 | * | 7/2007 | Wakabayashi et al. | ....... | 600/459 |
| 2008/0312537 | A1 | * | 12/2008 | Hyuga | .......................... | 600/459 |

FOREIGN PATENT DOCUMENTS

| DE | 4015686 | 11/1991 |
| DE | 196 24 163 A1 | 1/1998 |
| DE | 19624163 | 1/1998 |
| EP | 0176136 | 2/1989 |
| EP | 0 693 262 A1 | 1/1996 |
| WO | WO 2004110558 | 12/2004 |
| WO | 2008151340 | 12/2008 |
| WO | 2010023653 | 3/2010 |

OTHER PUBLICATIONS

Extended European Search Report dated Sep. 9, 2010 of European patent application No. 10157051.3.
Communication pursuant to Article 94(3) EPC, mailed Nov. 14, 2012 in connection with European Patent Application No. 10157051.3.

* cited by examiner

*Primary Examiner* — Sanjay Cattungal
(74) *Attorney, Agent, or Firm* — Westman, Champlin & Koehler P.A.

(57) ABSTRACT

A high power ultrasound application device (1) is provided which comprises a hand-held applicator (3). The applicator comprises a converter element (5) for converting electric signals into ultrasound waves; a treatment head (6) configured to apply ultrasound waves from the converter element to a subject to be treated; a handle (8) for holding and manipulating the applicator; and an oscillator circuit (9) arranged in the applicator and comprising one or more electronic components (10A, 10B) configured to be energized by a power source and to generate an output signal to drive the converter element. The oscillator circuit is in thermal contact with the handle, and the handle comprises a heat conductivity and thermal coefficient such that, when manually held by an operator in normal use, a heat conductive channel is provided between at least a portion of the circuit and the operator.

12 Claims, 2 Drawing Sheets

ULTRASOUND APPLICATION DEVICE

CROSS-REFERENCE AND PRIORITY CLAIM TO RELATED APPLICATIONS

This application claims priority to European Patent Application No. 10157051.3, filed Mar. 19, 2010, entitled "Ultrasound application device" which application is incorporated herein by reference and made a part hereof in its entirety.

TECHNICAL FIELD

The present disclosure relates to the field of ultrasound application devices, in particular ultrasound application devices for physiotherapeutic use, more in particular to high power ultrasound application devices.

BACKGROUND

Ultrasound application devices are known for use in physiotherapy, e.g. for pain reduction but also for anti-stress and wellness therapy. Such devices comprise a hand-held applicator comprising a converter element for converting electric signals into ultrasound waves and a treatment head configured to apply ultrasound waves of the converter element to a subject, or patient, to be treated, as well as an oscillator circuit to generate an electric output signal to drive the converter element and a power source to drive the oscillator circuit.

Typically used ultrasound frequencies range between about 10 mHz to about 3 MHz. Generally, an ultrasound power density or intensity generated at the treatment head between about 0.05 and about 0.4 W/cm$^2$ is considered "low power", and an ultrasonic power density between about 0.8 to about 3 W/cm$^2$ is considered "high power". The useful surface area of the treatment head determines the total power deliverable or delivered to the subject and the total power to be delivered by the oscillator circuit to the converter element.

Ultrasound application devices for professional use generally comprise treatment heads with effective surface areas of several cm$^2$, e.g. about 5 cm$^2$. A high power device thus should deliver about 4-15 W ultrasound power. Presently, such powers can only be delivered by two-part devices comprising a power unit and a hand-held applicator coupled with a cable, wherein the power unit comprises the power source and the oscillator circuit, and the hand-held applicator comprises the converter element and the treatment head. The output signal of the oscillator circuit must be transmitted through the cable. Even an efficient oscillator circuit generates heat so that the power unit requires a cooling system; for high power operation several Watts of thermal energy have to be siphoned off to prevent the oscillator circuit from overheating.

EP 0 176 136 discloses an ultrasound application device, which comprises an adjustable element provided in a treatment head, the adjustment of which indicates the efficiency and the impedance of the converter element, and a controlling circuit being provided for influencing the electrical output signal in dependence on the adjustment of the adjustable element in such a manner that the treatment head delivers ultrasound waves with the desired intensity.

Although operating successfully the device and the effort required for adjusting the adjustable element and possible associated recalibration of (portions of) the device are considered complex. A simpler, preferably more energy-efficient, device is therefore desired.

US 2004/0171970 and DE 40 15 686 teach that energy consumption of an ultrasound device may be reduced to a point where the device may comprise an integrated battery-operated hand-held applicator by reducing the ultrasound output power by intermittent interruption of the output power. The effectively delivered ultrasound power over the course of a treatment is thus a fraction of the stated power and intensity. This restricts usability of the devices which is undesirable for professional medical and/or physiotherapeutic practice.

Further, DE 196 24 163 discloses an ultrasound system comprising a compact unit housing the entire therapy system and coupled to the external current supply via a network plug. A microcomputer controls the overall operation of the therapy system.

WO 2004/110558 discloses an ultrasonic skin care device having an applicator head for applying the ultrasound vibrations to a user's skin. The applicator head has a vibrator element and a horn which are integrated into a combined vibration mass that resonates with an electric pulse to produce the ultrasound vibrations. The device is configured to limit the ultrasound upon detection that the applicator head is out of a normal contact with the skin. Consequently, there is a desire for an improved high power ultrasound application device.

SUMMARY

In view of the above-described problems a high power ultrasound application device according to claim 1 is provided. Since the oscillator circuit is comprised in the hand-held applicator itself, the oscillator circuit may be connected directly to the other components of the applicator without requiring adjustment associated with a cable and/or transfer functions as in EP 0 176 136. This facilitates the device and possible calibration procedures. It also reduces power consumption of the application device allowing use of a less powerful oscillator circuit for generating substantially the same ultrasound output intensities and powers, e.g. since losses due to a cable and a filter between a power unit and the applicator are also reduced and/or an adjustment element is obviated. A filter is usually applied to reduce emission of electromagnetic radiation by such cable from higher orders and general noise.

The thermal coupling via the handle between the oscillator circuit and the operator holding the handle enables the use of the operator as a heat sink for heat produced by the oscillator circuit, which provides improved cooling of the circuit, allowing the circuit—and thus the device—to be operated at elevated power and for extended periods without the risk of overheating the circuit and/or the converter element.

It has been found by the applicant that an average human holding an object forms such a surprisingly efficient heat sink that, together with the incorporation of the circuit in the applicator, an ultrasound device may be achieved which is capable of operating in the high power regime for extended periods of time.

To improve usefulness and user comfort the handle is optimized in that a balance is struck between heat conductivity and heat capacity of the handle which allows transmitting/drawing off heat at a convenient rate for the circuit and distribution of the heat over the handle such that an operator is comfortable with gripping and holding the handle, e.g. preventing localized thermal differences such as "hot spots" or "cold spots" and/or a—real or imaginary—risk of burning. For this, at least a portion of the handle comprises an inner layer of a material with a first, relatively high, thermal conductivity and an outer layer with a second, relatively low, thermal conductivity. The inner layer is arranged towards a portion of the circuit, e.g. in close thermal contact and/or in direct physical contact with a portion of the circuit, and serves for deferring and redistributing heat from (the hottest components of) the circuit. The outer layer is arranged exterior of the inner layer with respect to the circuit, possibly being an outer layer or providing an outer surface of the handle, and is provided for even, gradual and/or non-local dispensing and/or drawing off of the heat from the inner layer. The outer layer may be configured for gripping and holding the applicator and may indicate one or more preferred holding portions such that, when manually held in that position, the heat conductivity of the applicator is optimized, e.g. the channel being shortest. One or more further layers interior of the inner layer and/or exterior of the outer layers may be provided.

The handle may comprise a substantially enclosed electrically conductive shell, to reduce emission of electro-magnetic noise ("EM noise") from the applicator. In a device comprising a cable through which oscillating electrical fields and/or ultrasound signals are transmitted, care must be taken to shield the cable against emission of EM noise. This may require filtering which inherently causes significant losses. Since the circuit is comprised in the present applicator, such transmission is substantially absent and, correspondingly, filtering of the signal and/or shielding of a cable are obviated. A filter may be absent and any cable may be consequently be lighter-weight and more flexible, reducing energy and/or material consumption and improving operator comfort.

Suitably, at least a portion of the inner layer is metallic, e.g. a metallic shell, and at least a portion of the outer layer is a non-metallic cover, which may substantially cover the entire handle. The metallic shell provides an electrically conductive shell acting as an EM shield. Further, the applicator provides a suitable heat conductive channel when it is held in different positions and/or grips, e.g. in a fist grip with all fingers and the hand wrapped around the handle or in a pen grip between thumb and forefingers, with the treatment head being distal or proximal from the handle with respect to the operator. The metallic material may be a substantially pure metal, e.g. aluminum or copper, an alloy, e.g. brass or steel, and/or an assembly of layers of different materials and/or compositions. Pure metals tend to have higher thermal conductivity than alloys, whereas alloys tend to have greater heat capacity; an assembly of layers may be used to tune the thermal properties of the handle portion under consideration.

The non-metallic outer material prevents direct contact to the metallic portion, preventing perceiving hot spots or cold spots. The non-metallic cover may be a substantially unitary or monolithic object, e.g. a shell molded, wrapped or shrunk around and onto the metallic shell. The non-metallic cover may hold a multi-part metallic shell together. A unitary be treated. A smooth surface may improve hygiene. A unitary cover may also improve liquid tightness of the applicator. Suitable non-metallic materials comprise plastics and foams.

The device may comprise a detection system for detecting one or more predetermined operating conditions, in particular sub-optimal operating conditions, of the device and a control circuit for adapting the operating conditions and/or generating a warning signal. Sub-optimal operating conditions may originate from various causes. Examples include lack of desired resonance conditions between the oscillator circuit and the converter element, insufficient contact between the treatment head and a subject to be treated, a too high or a too low temperature of one or more portions of the device, etc. Reduced contact between the treatment head and a subject to be treated may reduce the impedance for transfer of the ultrasound energy to the subject and thus affect the resonance properties of the applicator. Also, heating and/or cooling of the converter element may change its resonance frequency and thus its acceptance of the output signal of the oscillator circuit and therewith the energy efficiency of the oscillator circuit and the device as a whole. Loss of efficiency may lead to heating of the oscillator circuit, affecting its operation efficiency and to heating of the applicator as a whole. This may cause an undesirable runaway effect. Detecting a resonance condition and deviation from it may be done in any known manner.

Operating conditions may be adapted in various ways. One way is to reduce the energy consumption of the oscillator circuit and/or the output energy of the applicator. This is effective but may be undesired for particular therapies.

Another way is to vary the operating frequency of the output signal of the oscillator circuit so as to tune the output signal frequency to the resonance frequency of the converter element. For particular therapies, particular ultrasound frequencies are desired. However, some frequency deviation (bandwidth) is generally acceptable; a frequency variation may have significantly less effect than an intensity variation so that treatment accuracy, e.g. administered ultrasound energy (e.g. accumulated dose in Joules), is more accurately determined. Tuning the output signal frequency to the resonance frequency of the converter element within the allowable frequency bandwidth therefore ensures effective treatment and energy efficient operation of the device. Improved energy efficiency results in reduced thermal load on the oscillator circuit and thus prolonged operation of the device.

The detection system and control circuit may be configured to maintain the temperature of at least a portion of the surface of the applicator, preferably substantially the entire surface or even the entire applicator, below a predetermined temperature, e.g. about 45 or about 40 degrees Celsius, in particular the treatment head and a gripping portion of the handle. Skin contact to warmer surfaces is generally unpleasant or harmful.

In particular for warning against insufficient contact with a subject to be treated direct operator feedback by an optical and/or acoustic warning signal may be more suitable than adaptation of operating conditions. Optionally a portion of the applicator may provide a vibration as a warning signal. The handle and the treatment head may be separated by an insulating portion, for insulating the portions electrically, thermally and/or (ultra-)acoustically. The applicator may comprise one or more light sources and the insulating portion may comprise a substantially translucent or transparent portion configured to transmit light from the light source(s). The one or more light sources may be used to indicate an operating condition and/or convey a warning signal. In addition and/or alternatively the light may be used for illuminating a portion or treatment zone of a subject to be treated.

To facilitate use of the device for different treatments, the device may be configured for emitting ultrasound at least two different ultrasound frequencies, which may be selectable on the device from a range of predetermined frequencies. Preferred ultrasound frequencies comprise about 1 MHz and about 3 MHz.

The device may further be configured for applying electrotherapy.

The oscillator circuit may comprise a (micro)controller and a frequency generator controlled by the (micro)controller. This allows accurate determination and adjustment of the ultrasound frequency. Accurate adjustment allows fine tuning the frequency of the output signal to maintain a resonance condition and minimize losses. Optionally a filter is provided.

A hand held applicator may be manufactured and/or sold as an independent apparatus for exchange, upgrading and/or adapting an ultrasound application device as described herein.

BRIEF DESCRIPTION OF THE DRAWINGS

The above-described aspects will hereafter be more explained with further details and benefits with reference to the drawings showing an embodiment of the invention by way of example.

Figure 1:
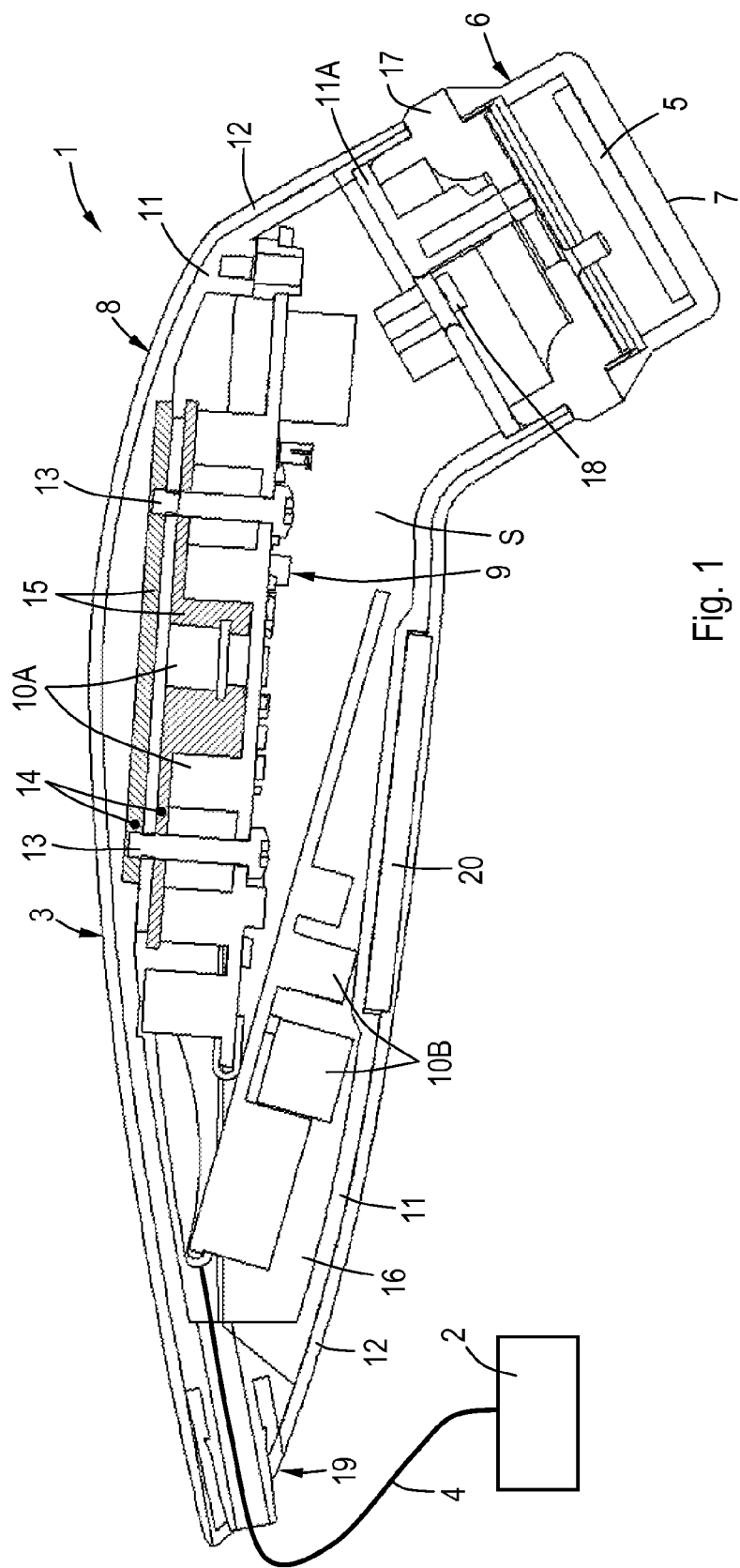
FIG. 1 is a schematic drawing of an ultrasound device, comprising a schematic cross-section view of an applicator.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral.

DETAILED DESCRIPTION OF EMBODIMENTS

FIG. 1 shows an ultrasound application device 1 comprising a power source 2 and a hand-held applicator 3 coupled with the power source 2 via a cable 4. The power source 2 may be part of a larger system, possibly comprising controls for the applicator 3. The applicator 3 comprises a converter element 5, e.g. a piezo crystal, for generating ultrasound waves, a treatment head 6 configured to apply ultrasound waves of the converter element 5 via a treatment surface 7 for contacting a body portion of a subject to be treated (not shown) to the subject. The applicator 3 further comprises a handle 8 for manually holding by an operator, e.g. a physiotherapist, and manipulating the applicator 3. The handle 8 is a hollow object providing an interior space S. An oscillator circuit 9 is arranged in the interior space S of the handle 8, in turn comprising one or more electronic components 10A, 10B configured to be energized by the power source 2 and to generate an output signal to drive the converter element 5.

The treatment head 6 may be of metal, suitably it is of aluminum. The treatment surface 7 may comprise an effective surface area, e.g. determined by the size, efficiency and configuration of the converter element 5, of several square centimeters, e.g. about 5 cm$^2$, but larger or smaller surface areas are conceivable. A metallic treatment head 6 which is conductive further facilitates providing pulsed or continuous electrotherapy to the subject to be treated via the applicator 3, either alone or in combination with ultrasound therapy. In the latter case it is ensured that both ultrasound energy and electrical energy are applied to the exact same treated location. The applicator 3 may comprise one or more connectors for connecting to a power source for electrotherapy, either directly on the treatment head 7 or elsewhere on or in the applicator 3.

The handle 8 is formed for convenient holding by an average adult human hand in one or more grips. By means of a design of the handle, regarding shape and/or use of (portions of) materials, one or more particular grips, e.g. grips in a particular location and/or grips providing a relatively large direct contact area between the hand of the operator and the handle such as a fist-grip, may be suggested and/or promoted for optimizing heat transfer.

The handle 8 comprises a metallic inner layer 11, having a relatively high thermal conductivity, and a non-metallic, e.g. plastic, outer layer 12 with a relatively low thermal conductivity. The inner layer 11 is formed as a metallic shell, here in the form of two joined half-shells. The inner layer 11 may be formed of aluminum which may readily be worked (e.g. by casting, milling, lathing, sawing, drilling, welding, etc.) and has high thermal and electrical conductivity. The handle 8 comprises an outer layer 12 in the form of a monolithic plastic object molded onto the metallic shell 11. In the shown embodiment, the oscillator circuit 9 is in close thermal contact with the inner layer 11 of the handle 3 by being in direct physical contact with it and being fixed to it with screws 13, but any other suitable manner may be employed e.g. with one or more clamps or rivets or and/or using gluing, welding and/or soldering techniques etc. To improve the heat transfer capacity of the applicator, spaces 14 between the inner layer 11 and electronic components 10A that generate heat in particular are filled with one or more thermal conductors, i.e. materials and/or objects 15 having elevated thermal conductivity, e.g. so-called gap pads and/or thermally conductive pastes which are optimized for transmitting heat, known per se. Spaces 16 between electronic components 10B which generate little or no heat and/or which may require direct access, such as adjustable capacitors or potentiometers, may be left open.

Between the electronic components 10 and an outer surface of the outer layer 12 of the handle 8 a heat conductive channel is established via the components 10A, the thermal conductors 15, the inner layer 11 and the outer layer 12. When manually held by an operator, (the hand and body of) the operator can effectively operate as a heat sink for heat produced by (the components 10A of) the circuit 9.

The treatment head 6 and the handle 8 are separated by an optional insulating portion 17 here in the form of a plastic translucent ring 17 around the applicator 3. The ring 17 provides electrical, thermal and ultra-acoustical insulation between the treatment head 6 and the handle 8. On the interior side of the ring 17 within the handle 8 a number of light sources 18 is arranged, e.g. LEDs which indicate operation conditions of the device 1 and/or other information; e.g. green or amber light or continuous light for "OK" and red light and/or flashing light for "alert". Since the ring 17 extends around the applicator, such light is visible from plural angles and fully obscuring the light by a particular grip is prevented. This improves operational safety of the device.

The applicator may comprise one or more means, e.g. O-rings, for rendering the applicator substantially liquid tight and/or submersible for treatment in damp areas or under water. In the shown embodiment, rubber O-rings are arranged (not indicated) at the connections between the treatment head 6, the ring 17 and the handle 8. Similarly, a connection portion 19 for coupling with the cable 4 is formed such that the cable 4 may be fixed to the applicator 3 and be surrounded with a water-tight cable boot (not shown). Alternatively, a cable boot may be integrally formed with a portion of the outer layer.

The converter element 5 is attached to and electrically connected with the treatment head 6, e.g. with an electrically conductive glue and is electrically connected with the circuit 9 by one or more wires and/or springs (not shown). A conductive baffle 11A may be provided in the handle 8 near the treatment head 6 to further electrically enclose the interior space S of the handle 8 and to prevent EM noise escaping via an electrically insulating ring 17.

The shown applicator 3 comprises a magnetizable metallic strip 20 for fixing the applicator 3 to a magnetic object, e.g. in a cradle (not shown). The applicator itself may also comprise a magnet. The applicator 3 may further comprise one or more inputs, controls and/or further output devices such as a display, one or more further light sources (e.g. LEDs) and/or acoustic signal sources.

Figure 2:
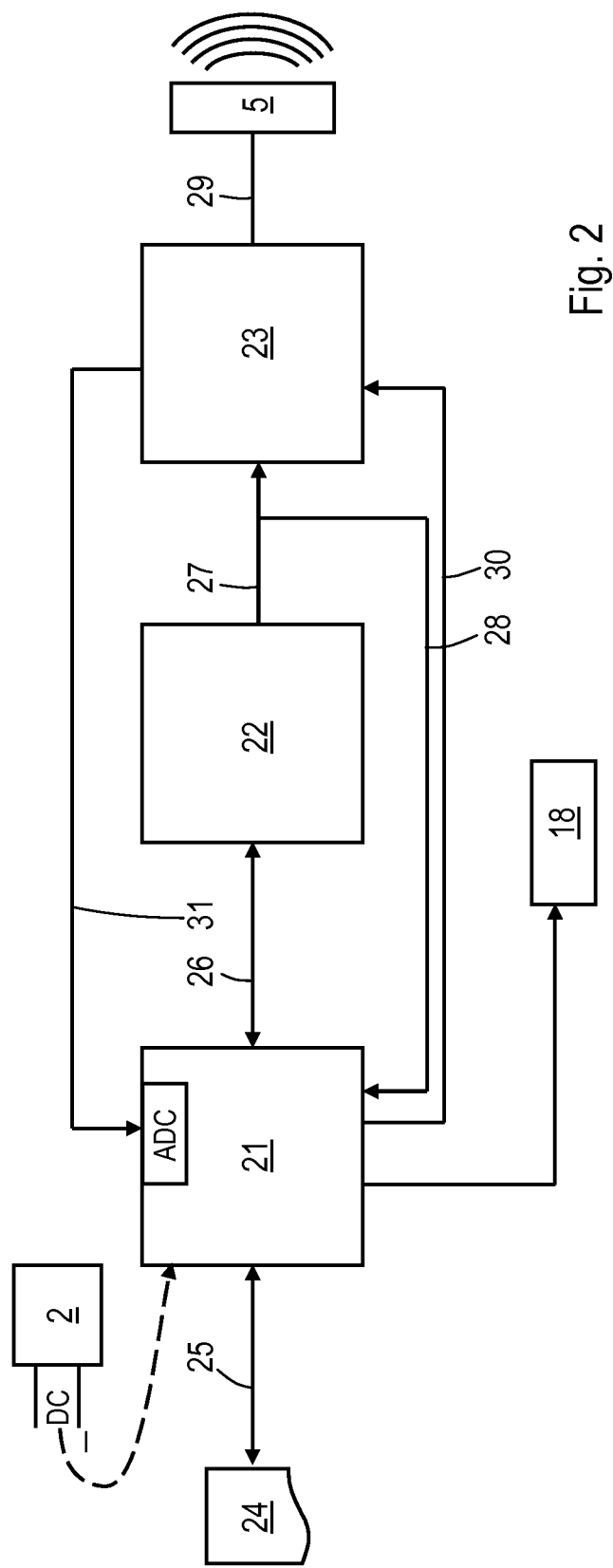
FIG. 2 indicates a block scheme for operation of the ultrasound device.

Operation of the device 1 will be further explained with reference to FIG. 2. The circuit 9 comprises a microcontroller 21, a frequency generator 22, and an optional output device 23 which may comprise inter alia a filter and/or an amplifier. Further components may be provided. The circuit 9 is electrically powered by the power source 2; DC power is preferred for reduction of EM noise and compatibility with battery-delivered power. In some embodiments the applicator 3 may be battery-fed, e.g. with one or more possibly rechargeable batteries suitably contained within the applicator 3.

The microcontroller 21 is controllable and/or programmable via a user interface 24 (using any suitable kind of transmission channel 25, e.g. wire based or wireless), which may be comprised in the applicator 3, an independent unit and/or the power supply 2. The user interface 24 may comprise one or more indicators for device status information and/or operation conditions. Here the microcontroller 12 further operates the light source 18 as a separate indicator.

In use, the frequency generator 22 is controlled by the microcontroller 21 (via a suitable transmission channel 26) and generates an oscillating electrical signal 27. The signal 27 may comprise plural frequencies. Present-day frequency generators may generate numerous, substantially freely selectable frequencies between e.g. about 1 kHz and 10 MHz with bandwidths of minute fractions of the selected centre frequency. From the frequency generator 22 a feedback signal 28 is sent to the microcontroller 21, e.g. a portion of the output signal, for controlling operation. The output signal 27 of the frequency generator 22 is sent to the output device 23 which transmits a modified signal 29, possibly filtered and/or amplified to the converter element 5. Operation of the output device 23 is also controlled by the microcontroller 21, e.g. for adjusting oscillation amplitude (transmission channel 30).

The output device 23 may comprise an impedance matching circuit, and/or measuring devices, e.g. a current monitor, a voltage monitor, a thermometer and/or a reflectometer for measuring reflection of the power sent to the converter element 5; data measured by the measuring devices is sent back to the microcontroller 21 (via a suitable transmission channel 31), here being converted from analogue to digital signals, for controlling and possibly adapting operation of the device.

In a typical professional ultrasound application device the treatment head has an active treatment surface area of approx. 5 cm$^2$. At a typical delivered power of approx. 2 W/cm$^2$ continuous output power, a total output power of about 10 W should be generated.

In a conventional ultrasound application device, to deliver 10 W ultrasound power, requires 18 W electrical input power: approx. 2.5 W power is typically lost at the converter element 5 (even at optimum resonance conditions) and approx. 5.5 W is lost in electronics, filtering and cables. Thus a total electrical-to-acoustical efficiency of approx. 56% is achieved under optimum operating conditions.

The losses are transformed in heat which must be drawn off. The losses in the converter element 5 are usually absorbed by the subject and may be used to advantage by providing a comfortably warm treatment surface. The losses in the electronics etc. produce so much heat that cooling systems are generally applied, which further reduce the overall energy efficiency of the device.

In the present device, to deliver 10 W ultrasound power, only 15.5 W electrical input power is required: again approx. 2.5 W power is typically lost at the converter element (even at optimum resonance conditions) but losses in the circuit 9 could be reduced to approx. 3.5 W in a first prototype. Thus a total electrical-to-acoustical efficiency of approx. 65% is achieved. This is a 16% increase in relative overall efficiency. The increase of the electrical energy transmission efficiency between the electrical input power and the power delivered to the converter element 5 is even as high as 83%. It is believed that in a further development additional optimization may be achieved, still further improving energy efficiency and reducing thermal load on an operator.

With a higher or lower power output power, either continuous, pulsed or using a fractional duty cycle having a duty cycle oscillating between a first power and a reduced but non-zero second power, e.g. 50% of the first power, and/or a higher or lower operating efficiency these numbers scale accordingly.

A handle 8 having an inner layer 11 of approx. 2 mm die cast aluminum and an outer layer of approx. 2 mm plastic, (e.g. polyethylene or polyvinylchloride), with a gap pad 15 of about 3 mm in relaxed state compressed to approx. 1 mm thickness and bridging a gap 14 between a heat generating transistor and held by an average adult human hand in fist grip allows drawing off approx. 3.5 W. Such device is operable with continuous emission of ultrasound energy well above approx. 0.8 W/cm$^2$ for any desired time. In a prototype, an output power of approx. 2 W in continuous operation could be maintained continuously with the temperature of the handle remaining below 45 degrees Celsius in free air. When held in a hand, the temperature of the handle dropped further. It is expected that approx. 3 W/cm$^2$ in pulsed operation with an on-off duty cycle of approx. 90% on (emitting) and 10% off (non-emitting) could also be maintained for any desired duration with the temperature of the handle remaining below 45 degrees Celsius in free air. With an increased or a reduced power, either continuous, pulsed or using a fractional duty cycle having a duty cycle oscillating between a first power and a reduced but non-zero second power, e.g. 50% of the first power, the device may be operable scaled accordingly.

The described device is particularly suited for operation in the high power regime, but it may also be operable at significantly lower powers. Utilizing a (micro-)controlled frequency generator, in particular with feedback, facilitates accurate control over frequencies to be emitted throughout vast frequency ranges and vast power ranges.

The invention is not restricted to the above described embodiments which can be varied in a number of ways within the scope of the claims. For instance the applicator may have another shape and/or may comprise further functions.

The device may comprise a timer and/or power detector for determining an administered dose of ultrasound energy, possibly accounting for cumulative effects.

A memory may be provided in conjunction with the microcontroller for storing (possibly) predefined treatments and/or protocols.

Elements and aspects discussed for or in relation with a particular embodiment may be suitably combined with elements and aspects of other embodiments, unless explicitly stated otherwise.

The invention claimed is:

1. A high power ultrasound application device comprising:
    a hand-held applicator comprising:
        a converter element for converting electric signals into ultrasound waves;
        a treatment head configured to apply ultrasound waves from the converter element to a subject to be treated;
        a handle for holding and manipulating the applicator; and
        an oscillator circuit arranged in the applicator and comprising one or more electronic components configured to be energized by a power source and to generate an output signal to drive the converter element;
        wherein spaces between an inner layer of the handle and one or more electronic components are filled with one or more thermal conductors, such that the oscillator circuit is in thermal contact with the handle and a heat conductive channel is provided between at least a portion of the circuit and an outer layer of the handle configured to direct heat from at least a portion of the circuit towards an operator holding the outer layer of the handle during operation.

2. The ultrasound application device of claim 1, wherein at least a portion of the handle comprises an inner layer of a material with a first thermal conductivity and an outer layer of a material with a second thermal conductivity, wherein the first thermal conductivity is higher than the second thermal conductivity.

3. The ultrasound application device of claim 1, wherein the handle comprises a substantially enclosed electrically conductive shell.

4. The ultrasound application device of claim 1, wherein the handle comprises a metallic shell and a non-metallic cover covering at least a portion of the metallic shell.

5. The ultrasound application device of claim 4, wherein the non-metallic cover is a substantially unitary object.

6. The ultrasound application device of claim 1, wherein the device comprises a detection system for detecting one or more predetermined operating conditions of the device and a control circuit for adapting the operating conditions and/or generating a warning signal.

7. The ultrasound application device of claim 6, wherein the device comprises a detection system for detecting a contact status of a contact between the treatment head and a subject to be treated.

8. The ultrasound application device of claim 1, wherein the handle and the treatment head of the applicator are separated by an insulating portion.

9. The ultrasound application device of claim 8, wherein the applicator comprises one or more light sources and the insulating portion comprises a substantially translucent or transparent portion configured to transmit light from the one or more light sources.

10. The ultrasound application device of claim 1, wherein the device is configured for emitting ultrasound at at least two different ultrasound frequencies.

11. The ultrasound application device of claim 1, wherein the oscillator circuit comprises a microcontroller and a frequency generator controlled by the microcontroller.

12. Applicator for use in a high power ultrasound application device, which is couplable with a power source and comprises:
- a converter element for converting electric signals into ultrasound waves;
- a treatment head configured to apply ultrasound waves from the converter element to a subject to be treated;
- a handle for holding and manipulating the applicator; and
- an oscillator circuit arranged in the applicator and comprising one or more electronic components configured to be energized by a power source and to generate an output signal to drive the converter element;
- wherein spaces between an inner layer of the handle and one or more electronic components that are filled with one or more thermal conductors, such that the oscillator circuit is in thermal contact with the handle and a heat conductive channel is provided between at least a portion of the circuit and an outer layer of the handle configured to direct heat from at least a portion of the circuit towards an operator holding the outer layer of the handle during operation.

* * * * *